Figure 1A:
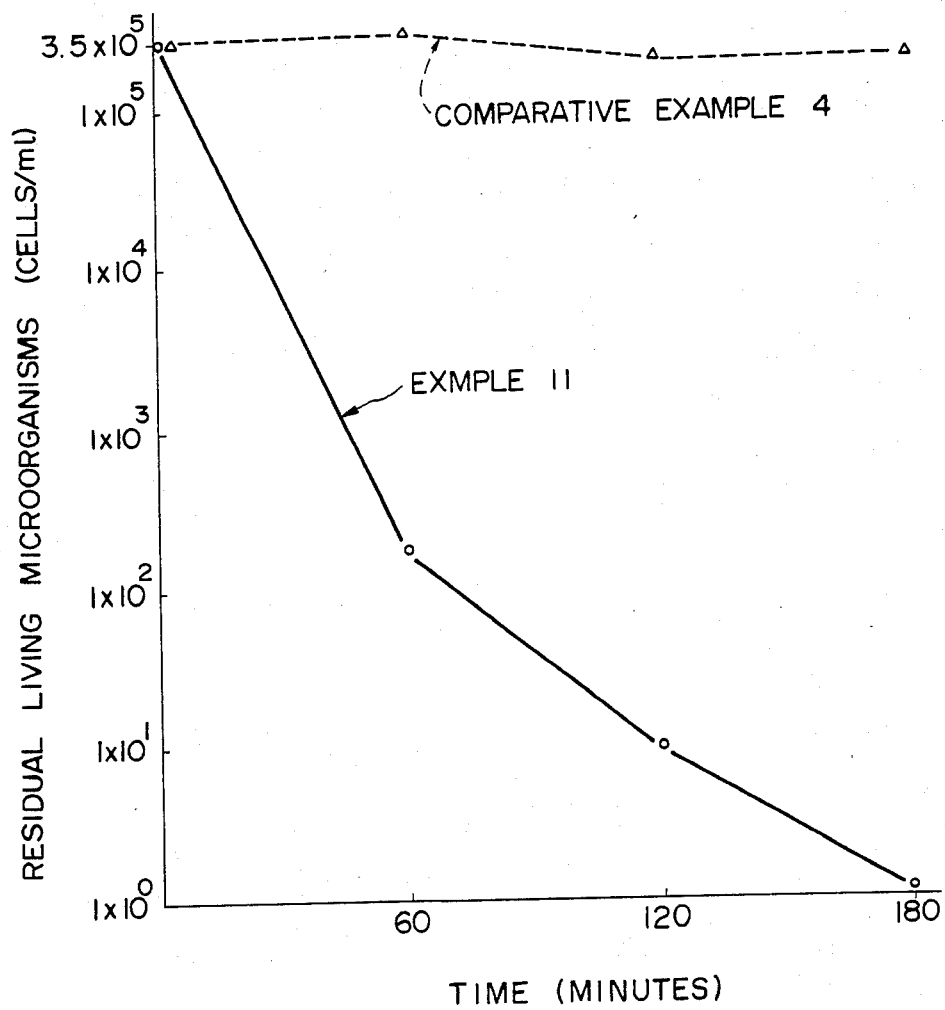

United States Patent [19]

Yoshino et al.

[11] Patent Number: 4,520,072
[45] Date of Patent: May 28, 1985

[54] HETEROGENEOUS SYSTEM PHOTOSENSITIVE OXIDATION SENSITIZER

[75] Inventors: Akira Yoshino, Fujisawa; Isamu Iwami, Zushi, both of Japan

[73] Assignee: Asahi-Dow Limited, Tokyo, Japan

[21] Appl. No.: 363,607

[22] Filed: Mar. 30, 1982

Related U.S. Application Data

[63] Continuation of Ser. No. 121,586, Feb. 14, 1980, abandoned.

[30] Foreign Application Priority Data

Feb. 28, 1979 [JP] Japan .................................. 54-21829
Aug. 27, 1979 [JP] Japan ................................ 54-108156
Nov. 7, 1979 [JP] Japan ................................ 54-143241
Nov. 7, 1979 [JP] Japan ................................ 54-143242

[51] Int. Cl.³ .......................... B01D 39/08; B32B 5/16
[52] U.S. Cl. .................................... 428/403; 210/506; 210/679; 210/698; 430/339
[58] Field of Search ............... 210/508, 679, 680, 506, 210/698; 422/212; 428/403; 430/339

[56] References Cited

U.S. PATENT DOCUMENTS

| | | | |
|---|---|---|---|
| 3,951,797 | 4/1976 | Seely | 204/157.1 X |
| 3,997,483 | 12/1976 | Warster et al. | 210/679 X |
| 4,025,428 | 5/1977 | Wegmuller et al. | 210/679 |
| 4,079,001 | 3/1978 | Haase et al. | 210/679 |
| 4,234,652 | 11/1980 | Vanoni et al. | 210/508 X |

*Primary Examiner*—Michael R. Lusignan
*Attorney, Agent, or Firm*—Armstrong, Nikaido, Marmelstein & Kubovcik

[57] ABSTRACT

A compound selected from some classes of coloring substances having good resistance to light and oxidation is found to have a high photosensitive activity when it is supported in an actively dispersed form on a carrier. The sensitizer obtained is useful for heterogeneous system photosensitive oxidation for various purposes, for example, treatment of harmful organisms or impurities contained in the air or water. The sensitizer has also good resistance to light and oxidation and can be used repeatedly for a long time.

6 Claims, 8 Drawing Figures

HETEROGENEOUS SYSTEM PHOTOSENSITIVE OXIDATION SENSITIZER

This is a continuation of application Ser. No. 121,586, filed 2/14/80, now abandoned.

This invention relates to photooxidation by exposure to visible light using a novel sensitizer for photosensitive oxidation having excellent light resistance, oxidation resistance, water resistance and chemical resistance, including various uses thereof in such applications as purification of polluted air or water and inhibition of activities of harmful organisms.

As the method for carrying out photooxidative reaction using a sensitizer, there have been known a homogeneous reaction system and a heterogeneous rection system. In the former method, a sensitizer is employed as a homogenous solution with a substance to be oxidized. Hence, there ensue such disadvantages as difficult recovery of the sensitizer after the reaction by separation and environmental pollution caused by the effluent of the sensitizer out of the system.

In recent years, there is reported a basic principle that the reaction can proceed at a high efficiency even by use of a heterogeneous system sensitizer. For example, John R. Williams et al disclose photosensitizers comprising Rose Bengal, Eosin or Methylene Blue attached to ion-exchange resins (Tetrahedron Letters No. 46, pp. 4603–4606, 1973, Pergamon Press). Blossey et al also disclose photosensitizers comprising Rose Bengal or Eosin attached to chloromethylated polystyrene beads (Journal of the American Chemical Society Vol. 95, p. 5820, 1973). Furthermore, U.S. Pat. No. 3,951,797 discloses heterogeneous system sensitizers comprising basic dyes such as Methylene Blue or Toluidine Blue attached to hydrous gels of metal alginate. These methods are very attractive in commercial applications because the sensitizers can be used under heterogeneous conditions.

However, in any of the reaction system, the sensitizing substances conventionally used in the prior art are all insufficient in physical and chemical stability. That is, such conventional sensitizing substances as Rose Bengal, Eosin, Chlorophyllin, Haematoporphyrin, Thionine, Methylene Blue, Toluidine Blue or Fluorescene are entirely insufficient in such properties. During usage, they may suffer from such changes as light discoloration, oxidative deterioration or hydrolysis to thereby lose the sensitizing function in earlier stages. Thus, these substances had the vital defect as being practically inapplicable.

The substances well known in the art having photosensitive activity, including Rose Bengal, Eosin, Chlorophyllin, Methylene Blue, Toluidine Blue, etc. are inferior in such properties as light resistance, oxidative resistance, chemical resistance and water resistance. It would be rather antinomic to desire that a substance may have properties excellent both in photosensitive activity and in light resistance or oxidative resistance. Thus, it has been believed very difficult or impossible to obtain such a substance.

From such a standpoint, the present inventors have made extensive studies to obtain a sensitizer for heterogeneous system photosensitive oxidation which can stand prolonged use and re-use, having excellent light resistance, oxidative resistance and chemical resistance. As the result, it has been found that a coloring substance having a degree of discoloration in the range from the rating No. 4 to the rating No. 8 can be supported on a carrier in an actively dispersed form to provide an excellent sensitizer for heterogeneous system photosensitive oxidation exhibiting stable photosensitive activity. The present invention has been accomplished based on such a finding.

The sensitizer for heterogeneous system photosensitive oxidation referred to in the present invention comprises a sensitizing substance fixed in an actively dispersed form onto a carrier, which may be used in such heterogeneous systems as solid-gas phase, solid-liquid phase and solid-solid phase, depending on the phase of the material to be oxidized and the object of oxidation.

According to the present invention, there is provided a method for treatment of a system containing harmful substances and/or organisms by exposure to a visible light in the presence of oxygen using a sensitizer, being characterized in that said sensitizer comprises a coloring substance having a degree of discoloration in the range from the rating No. 4 to the rating No. 8, said substance being supported on a carrier in an actively dispersed form so as to have a $\Delta DO$ value of 0.5 or more.

The sensitizer as specified above to be used in the present invention is novel per se and can be used for various purposes including heterogeneous photooxidation reactions other than such a treatment as mentioned above.

According to the present invention, there is also provided a device for treatment of a system containing harmful substances and/or organisms, which is constituted of:

(a) a part comprising a sensitizer as specified above: and (b) a means for irradiating a visible light, said part (a) being arranged so as to be contactable with the system to be treated and said means (b) being arranged so as to be capable of effecting irradiation of the light over said part (a).

As mentioned above, the degree of discoloration of a sensitizing substance is a very important characteristic related to the light resistance and oxidative resistance in the present invention. Said characteristic may be evaluated in terms of the light resistance test value as determined by JIS Standard-LO841. Using Blue Scale as the standard, coloring substances can be evaluated and classified into eight ratings from the rating No. 1 to the rating No. 8. The rating No. 1 has the most inferior light resistance and the rating No. 8 the most excellent. As is well known in such fields as dye or pigment industry, plastic industry, paint industry, etc., various articles are desired to have a light resistance test value of at least 4 in order to stand uses in outdoors, namely under conditions of exposure to the rays of sunlight in an oxygen atmosphere. In fact, the sensitizing substance to be used in the present invention is also required to have a value of at least 4 so as to be durable in practical applications. As mentioned above, when a compound having a small light resistance value of 1 to 3 is used as a sensitizing substance, it may undergo light discoloration, oxidative deterioration at the outset of usage, thus failing to be practically used. Accordingly, it is required in the present invention to use a sensitizing substance having a value of 4 to 8, preferably 5 to 8. On the other hand, the sensitizing substances well known in the art are found in some of water soluble xanthene compounds, acrydine compounds, thiazine compounds, triphenylmethane compounds and phenadine compounds. All of these compounds have inferior light resistance and oxidation resistance. For example, typical sensitizing substances such as Rose Bengal, Eosin and Fluorescene belong to the lowest class of the rating No. 1. Even Methylene Blue, which is regarded as having excellent light resistance, belong to the rating No. 3. It should be noted that the sensitizing ability and the light resistance were contradictory to each other in the above group of compounds. In other words, a compound having good sensitivity is liable to have a very poor light resistance, while a compound having good light resistance has no sensitivity at all. Such a tendency may well be understood, since a sensitizing substance is a kind of an oxidation catalyst which cannot help being itself oxidized simultaneously with oxidation of a material to be oxidized and therefore better sensitizing activity means worse light resistance or oxidation resistance.

The present inventors have established a very rapid and accurate method for evaluation of photosensitive activity. As the result of measurement of a great number of compounds, there can be found a sensitizing substance excellent in photosensitive activity and also in light resistance or oxidation resistance from a very wide range of compounds. That is, some compounds belonging to the group of compounds having excellent light resistance and oxidation resistance, which do not exhibit any photosensitive activity when allowed to be present in the system alone, for example, as suspended agglomerates, are found to have absorption bands in the region of wavelengths from 380 nm to 800 nm and exhibit a high degree of photosensitive activity of 0.5 or more, sometimes 5 or more, in terms of the dissolved oxygen consumption value $\Delta DO$, when they are carried in an actively dispersed form on a carrier, thereby providing a sensitizer for heterogeneous system photosensitive oxidation having both excellent photosensitive activity and excellent light resistance.

The dissolved oxygen consumption value $\Delta DO$ referred to in the present invention is a value indicating a measure of a photosensitive activity of a sensitizing substance. It can be determined by dissolving a predetermined material to be oxidized in water having dissolved a certain concentration of oxygen therein and irradiating a certain intensity of light on the solution in the presence of a sensitizer. The percentage of dissolved oxygen decreased is defined by the following formula and can readily be measured by use of the testing apparatus as hereinafter described.

$$\Delta DO = \frac{DO_0 - DO_1}{DO_0} \times 100$$

wherein $DO_0$ is the dissolved oxygen amount before the reaction, $DO_1$ the dissolved oxygen amount after the reaction and $\Delta DO$ the dissolved oxygen consumption value.

To describe briefly about the evaluation method, a predetermined amount of furfuryl alcohol as a material to be oxidized is dissolved in water and irradiation of light is effected over the solution in the presence of a sensitizer at a predetermined intensity by use of a standard white light source as determined by J15Z-8902 a predetermined period. If said sensitizer has a photosensitive activity, photosensitive oxidation reaction of furfuryl alcohol will proceed, whereby the oxygen initially dissolved in the solution will be consumed. Thus, by measurement of the dissolved oxygen amounts before and after the reaction, the photosensitive activity of said sensitizer can be evaluated quantitatively within a short time.

Such a dissolved oxygen amount can be measured by a titration method such as Winkler method or others, or by means of a dissolved oxygen meter. Especially, a dissolved oxygen meter enables rapid and accurate measurements.

The dissolved oxygen consumption value $\Delta DO$ as determined by the above evaluation method can be a good parameter for showing the photosensitive activity of a sensitizer for the following reason. That is, a sensitizer exhibiting a high $\Delta DO$ value according to the above evaluation method is found to exhibit an efficient photosensitive activity in other photosensitive oxidation reaction systems, while that with $\Delta DO$ value of approximately zero exhibits substantially no photosensitive activity in other photosensitive oxidation reaction systems.

The sensitizer of the present invention is desired to have a dissolved oxygen consumption value $\Delta DO$ as defined above of 0.5 or more, preferably 2.5 or more, most preferably 5 or more. With a $\Delta DO$ value less than 0.5, the photosensitive activity is too low, whereby a photo-irradiation is required to be effected for promoting desirable oxidation reaction for such a long time as unacceptable in commercial applications.

The coloring substance to be used in the present invention should have absorption bands in the region of wavelengths from 380 nm to 800 nm. Either a compound having absorption bands only in the region of wavelengths less than 380 nm, i.e. ultra-violet region, or a compound having absorption bands only in the region of wavelengths over 800 nm, i.e. infra-red region, has only very low photosensitive activity. Moreover, if such a compound is desired to be used, no visible light is available as a matter of course to a great disadvantage. Of course, said coloring substance may have absorption bands also in the region of wavelengths less than 380 nm or over 800 nm, insofar as it has absorption bands in the region of wavelengths from 380 nm to 800 nm. The position of the absorption band herein mentioned may readily be determined by measurement of electron spectrum. However, since such an absorption band generally exists as a broad peak, the absorption band should more strictly be defined in the present invention as a band having absorption maximum in the region of wavelengths from 380 nm to 800 nm, or as a band having an absorption coefficient $\epsilon$ as defined by the following formula of at least 1 in a part of the region of wavelengths from 380 nm to 800 nm even when there is no maximum absorption in said region.

$$\epsilon = A/(c \times b)$$

wherein A is an absorption degree, c the concentration represented by g/ml and b the light path length represented by cm.

According to the present invention, there have been discovered a number of sensitizing substances from a wide range of compounds subjected to the evaluation tests as described above, which have both excellent photosensitive activity as well as excellent light resistance or oxidation resistance, although both properties are in themselves contradictory to each other as hereinbefore mentioned. In particular, excellent sensitizing substances are found in the group of compounds which are insoluble in water and also in the group of compound which are insoluble in both water and conventional organic solvents.

Typical examples of the sensitizing substances may be classified into the following groups of compounds (a) to (h);

(a) aromatic ketone compounds and derivative thereof such as anthraquinone, 1-hydroxy-4-aminoanthraquinone, N,N'-dibenzoyl--1,4-diaminoanthraquinone, benzoanthrone, anthrimide, pyranthrone, violanthrone, iso-violanthrone, dibenzopyrenequinone, anthranthrone, acedianthrone, etc.:

(b) aromatic heterocyclic compounds and derivatives thereof such as arthraquinone carbazole, anthraquinone acridone, anthraquinone thiazole, anthraquinone thioxanthrone, anthraquinone oxazole, anthraquinone oxadiazole, dihydroanthraquinadiene, flavanthrone, benzoanthrone acridine, pyrazole anthrone, anthrapyrimidine, etc.;

(c) aromatic hydrocarbon compounds or derivatives thereof such as chrysene, coronene, perylene, etc.;

(d) azo compounds and derivatives thereof such as 2,4-dinitrobenzeneazo-β-naphthol, 2-nitro-4-trifluoromethylbenzeneazo-β-naphthol, 4-methyl-6-nitrobenzeneazo-62 -naphthol, 2-nitro-4-chlorobenzeneazo-β-naphthol, 4-chlorobenzeneazo-3-(2,4-dihydroxy)quinoline, etc.;

(e) indigo, thioindigo compounds and derivatives thereof such as indigo, 4,4',6,6'-tetrachloroindigo, 4,4',6'-tribromoindigo, 4,4'-dibromoindigo, thioindigo, 5,5'-dichloro-7,7'-dimethylthioindigo, 5,5'-diethoxythioindogo, etc.;

(f) aromatic nitro, nitroso compounds and derivatives thereof such as 2,4-dinitro-4-hydroxydiphenylamine, naphthol green B, 4,4'-dichloro-2,2'-dinitrodianilinomethane, etc.;

(g) phthalocyanine compounds and derivatives thereof such as phthalocyanine, copper phthalocyanine, cobalt phthalocyanine, zinc phthalocyanine, nickel phthalocyanine, etc.;

(h) condensates of aromatic hydrocarbons, aromatic amino compounds, aromatic nitro compounds or aromatic hydroxy compounds such as m-tolylene diamine, 2,4-dinitro-4'-oxydiphenylamine, o-toluidine indophenol, α,α'-dinitronaphthalene, anthracene, etc. with sodium polysulfide or sulfur, conventionally called as sulfur dyes.

It is very important to recognize in using such a sensitizing substance that said sensitizing substance alone can exhibit only very low photosensitive activity. For example, there is no photosensitive activity exhibited by a suspension having powders of said sensitizing substance suspended in an insoluble solvent. Perhaps, this may be due to so called concentration quenching phenomenon, although true mechanism remains to be elucidated. Therefore, it is necessary to fix said sensitizer in an actively dispersed form onto a carrier in order for the sensitizer to exhibit its function.

As described above, the sensitizer for heterogeneous system photosensitive oxidation according to the present invention can be prepared by fixing a sensitizing substance satisfying the requirements restricted by the present invention onto a carrier in an actively dispersed form. The term "actively dispersed form" to be used in the present invention is a concept obtained inductively from the photosensitive activity represented in terms of the aforesaid dissolved oxygen consumption value $\Delta DO$, which is required to be at least 0.5, and its precise structure has not yet been clarified. Perhaps, it is believed that each substance is dispersed in the order of active units which may be molecular or something like that. The sensitizing substance is not required to be present necessarily only on the surface of the carrier, but it may be present also in the central part of the carrier.

The carrier to be used in the present invention is not particularly limited and may include synthetic or natural polymers or modified products thereof such as polystyrene, polymethyl methacrylate, polyethylene, polyamide, polyacrylonitrile, polyvinylidene chloride, epoxy resin, phenol resin, cellulose and the like; inorganic substances such as glass, silica, alumina, titanium oxide, zeolite, kaolin, bentonite, etc.; and metals such as aluminum, iron, copper, zinc, etc. The carriers may be shaped in various forms depending on the intended uses, for example, powders, pellets, beads, sheets, films, baloons, foams, fibers, cloths, and others.

Among the carriers mentioned above, there may be selected suitable class of carriers depending on the specific purpose of use of the sensitizer. For example, when it is to be used in inhibiting activity of harmful organisms, the class of carriers bearing cation groups can advantageously be used to provide an improved effect. The cation groups mentioned in the present invention are inclusive of substantially dissociated cation groups such as

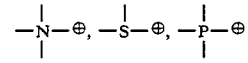

and metallic ions $M^{n+}$ and also of those having positive charges through polarization, although not completely dissociated, such as metal oxides, hydroxides, silicates, phosphates, borates, complex salts, etc. The carriers satisfying these requirements may be exemplified by the following groups (a) to (e).

(a) carrier originally provided with cation groups: anion exchange resin, vinyl pyridine hydrochloride polymer or copolymer, dimethylaminoethyl methacrylate hydrochloride polymer or copolymer, quaternary ammonium aminocellulose;

(b) carriers cationized by acid treatment or alkylation treatment of the following carriers: polyamine-cured epoxy resin, polyamide, melamine resin aminated cellulose, vinyl pyridine polymer or copolymer, dimethylamino ethylmethacrylate polymer or copolymer, aminopolystyrene polymer or copolymer, etc.;

(c) carriers modified with the following compounds having cation groups: γ-aminopropyl trimethoxysilane hydrochloride, trimethyldodecyl ammoniumchloride, triethylstearyl ammoniumchloride, β,γ-epoxy propyltrimethyl ammoniumchloride;

(d) carriers having incorporated metal cation groups by ion-exchange or neutralization of the following carriers: sulfonated polystyrene or copolymer, acrylic acid polymer or copolymer, natural polymers such as of alginic acid, etc.

(e) carriers having polarized positive charges without ionic dissociation: magnesium oxide, titanium oxide, aluminum silicate, calcium silicate, barium titanate, silica, alumina, vanadium oxide, etc.

In another application, wherein the sensitizer of the present invention is used for purification of water or air containing impurities, it is preferred to use a carrier having an apparent surface area A $CO_2$ of 0.1 m$^2$/g or more, as measured by the method as hereinafter described, for said sensitizer. The present inventors have investigated about the relation between an apparent surface area Ax calculated from the measured values of adsorption of various gases on the carrier such as nitrogen gas, argon gas, helium gas, etc. and its treatment function. As the result, a very good relation is found to exist only when carbonic acid gas is used as such a gas. It is not yet clear why a carrier having such properties bring about improved efficiency in photooxidation treatment. Such an increase in efficiency of photooxidation treatment may be estimated to be due to the effect of a material to be oxidized adsorbed in the vicinity of the carrier or due to the acceleration of the action of a sensitizing substance, i.e. photosensitive activity, by such a carrier. The apparent surface area A $CO_2$ herein mentioned is determined by measuring the adsorption capacity of carbon dioxide on a carrier using a conventionally used gas-adsorption surface area measuring instrument and calculating the measured value according to the BET method. Such a measuring method is conventionally used in measurement of surface area and the measurement can be very easy. The apparent surface area A $CO_2$ measured according to the method as mentioned above can be used as a parameter indicating photooxidation treatment efficiency of a carrier, as evidenced by the especially high efficiency exhibited in all the photooxidation treatments by use of carriers having a high value of A $CO_2$ according to the evaluation method.

Typical examples satisfying such requirements are activated charcoal, porous polymer gels of crosslinked polystyrene, crosslinked polymethacrylate, crosslinked cellulose, crosslinked nylon or others, porous glass, zeolite, molecular sieve, silica gel, activated alumina, diatomaceous earth, aluminum silicate, calcium silicate, magnesium silicate, oxides or hydroxides of titanium, zirconium, iron, cobalt, nickel, copper, magnesium, calcium, zinc, etc., weakly basic, moderately basic or strongly basic anion exchange type resins, fibers or membranes (among them, OH$^-$ type is especially preferred). The above carrier may be used singly or as a combination suitably combined. Furthermore, the above carriers may also be dispersed in a matrix.

The sensitizing substance can be dispersed and fixed on a carrier by any method whereby the sensitizing substance can be attached and fixed in an actively dispersed form onto the carrier. Depending on the sensitizing substance employed and the properties of a carrier, there may be used various methods as set forth below.

(1) A method in which a sensitizing substance is dissolved in an organic solvent or an inorganic solvent:

The sensitizing substance can be adsorbed on a carrier through impregnation, adsorption, dispersion or swelling by carrying out such procedures as dipping of the carrier in the solution or coating of the carrier with the solution. For most of the sensitizing substances as mentioned above, this method is applicable. Particularly, when there is employed (a) aromatic ketone compound, (b) aromatic heterocyclic compound, (c) aromatic hydrocarbon, (d) azo compound, (e) indigo or thioindigo compound, (g) phthalocyanine compound, or (h) sulfur dye compound, an inorganic solvent such as sulfuric acid, phosphoric acid, nitric acid or an aqueous alkali solution may advantageously be used as the solvent and the method can be applicable for both organic and inorganic carriers.

(2) A method wherein a sensitizing substance is blended together with a carrier by melting, dissolving or kneading:

This method is particularly effective when the carrier can be molded under a relatively low temperature or when the carrier is an organic substance readily soluble in a solvent. After blending, the blend can be shaped in any desired form. As one modification of this method, it is also possible to dissolve or molecular a sensitizing substance in monomers or pre-polymers, followed by completion of post-polymerization.

(3) A chemical precipitation method in which a sensitive substance is formed on a carrier;

This method is effective when the sensitizing substance is insoluble and influsible. The soluble precursor for said sensitizing substance is carried on a carrier and then the sensitizing substance is formed by such chemical reactions as coupling, condensation, cyclization, etc. This method is particularly effective when using as sensitizing substance (a) aromatic ketone compound, (b) aromatic heterocyclic compound, (d) azo compound, (e) indigo or thioindigo compound, or (g) phthalocyanine compound;

(4) Physical precipitation method such as vapor deposition:

The sensitizing substance is precipitated physically on a carrier by vapor deposition, ion-plating or spattering. Most of the aforesaid sensitizing substances are thermally very stable and hence it is particularly effective to use this method. As carriers for which this method can be used, there may be used any of the carriers as mentioned above, but this method is most suitable for metallic materials for which other methods can difficultly be applied.

(5) A method such as vat dyeing or sulfur dyeing in which a sensitizing substance insoluble in conventional solvents is made temporarily soluble by such a chemical reaction as reduction, supported on a carrier according to the method (1) and then returned to the original insoluble state;

This method is applicable for a sensitizing substance selected from (a) aromatic ketone compound, (b) aromatic heterocyclic compound, (e) indigo or thioindigo compound and (h) sulfur dye compound.

In each of the above methods, it is preferred to effect chemical bonding between the sensitizing substance and the carrier in order to support the sensitizing substance more strongly on the carrier.

For effecting support of the sensitizing substance on a carrier easily as well as firmly, the carrier may be subjected to oxidation, etching, treatment with a coupling agent or any other physical or chemical surface treatment.

The amount of a sensitizing substance supported on a carrier may sufficiently be very small and it is difficult to show the amount by weight. To venture to say, it may sufficiently be such that at least one of the color stimulation values, X, Y and Z as determined by JIS Z-8722 is 80 or less.

The sensitizer for heterogeneous photo-sensitive oxidation according to the present invention can be used in any reaction system of solid-gas phase, solid-liquid phase of solid-solid phase optionally selected depending on the state of the material to be oxidized under irradiation of light in the presence of oxygen or air, whereby the oxidation reaction can proceed with good efficiency. As the light source, there may be employed artificial light sources including tungsten lamp, fluorescent lamp, halogen lamp, metal halide lamp, xenon lamp, etc. There may also be used the sunlight.

As mentioned above, the sensitizer for heterogeneous system photosensitive oxidation of the present invention is obtained by having a sensitizing substance excellent in light resistance and oxidation resistance with a high photosensitive activity, which has not been known in the prior art, incorporated on a carrier. When it is provided for use as a means for synthetic chemistry, a means for oxidation treatment, a means for modification or a means for other oxidation reaction of various purposes, it can maintain its performance stably for a longtime, enabling commercially advantageous repeated uses for a long time.

Referring now to some examples of uses for which the sensitizer for heterogeneous system photosensitive oxidation can suitably be used, the present invention is illustrated in further detail below.

Figure 1B:
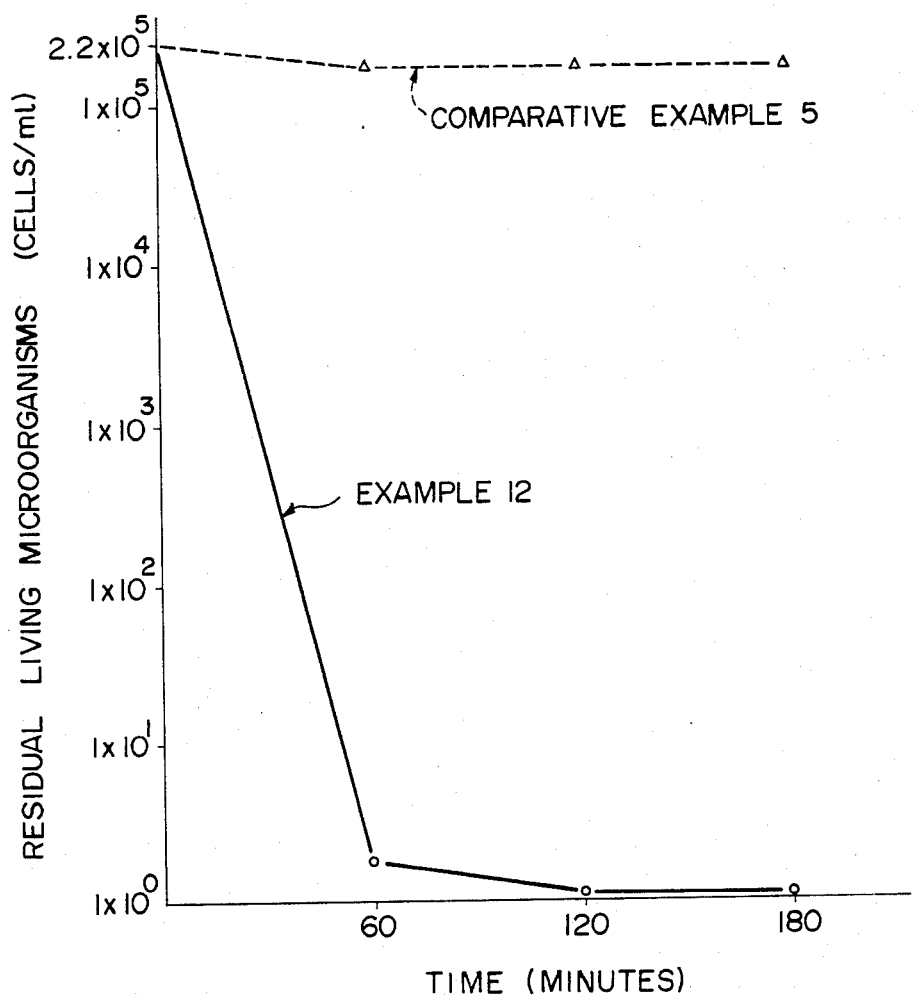
Figure 2:
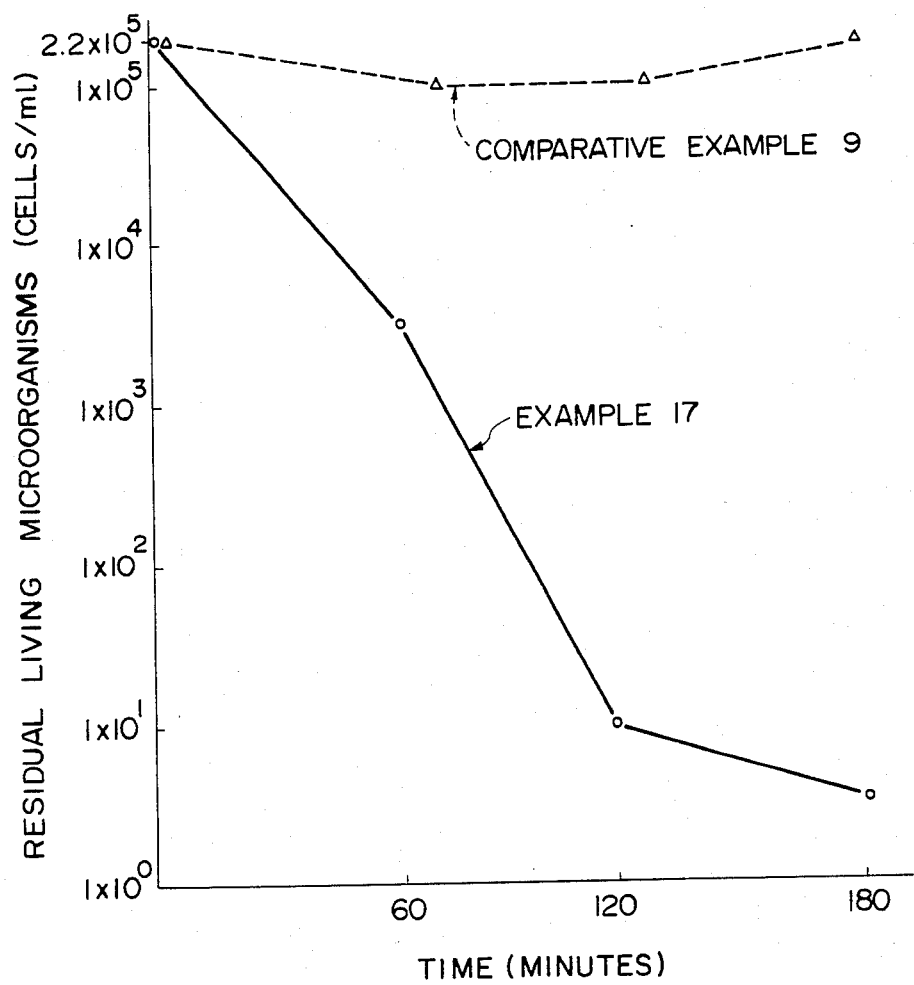
Figure 3:
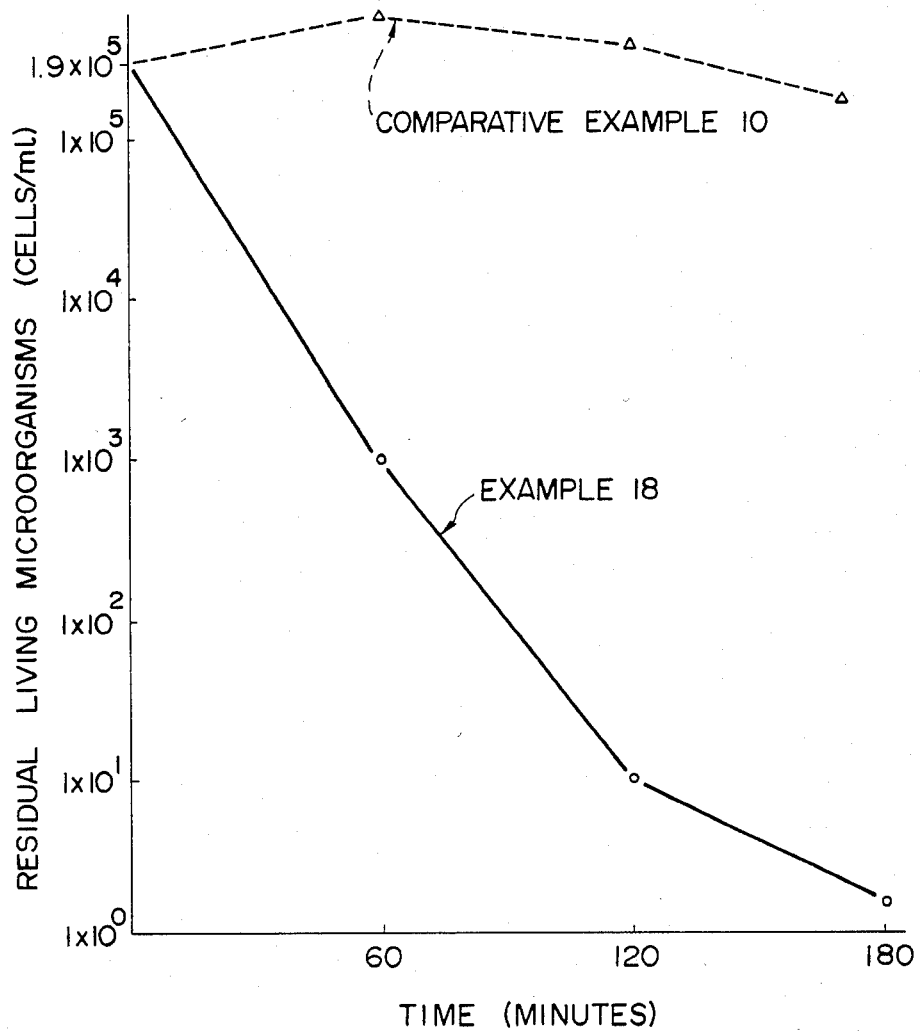
Figure 4:
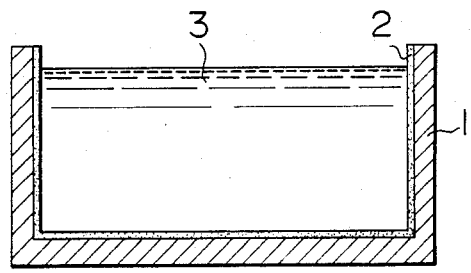
Figure 5:
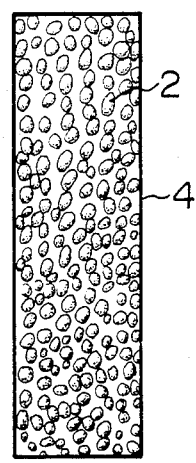
Figure 6:
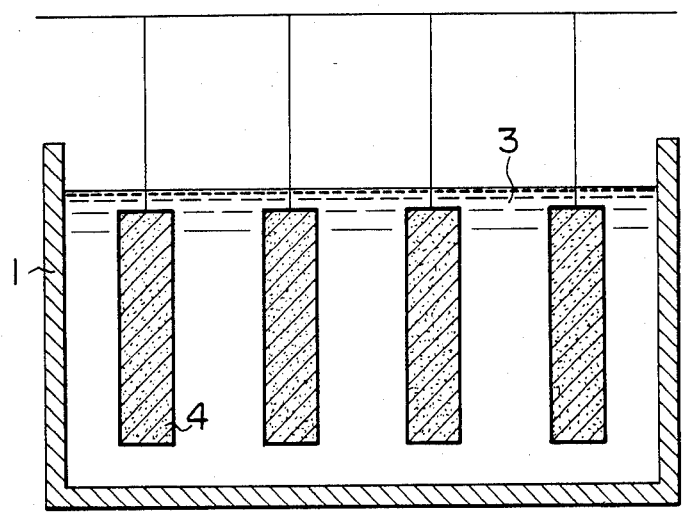
Figure 7:
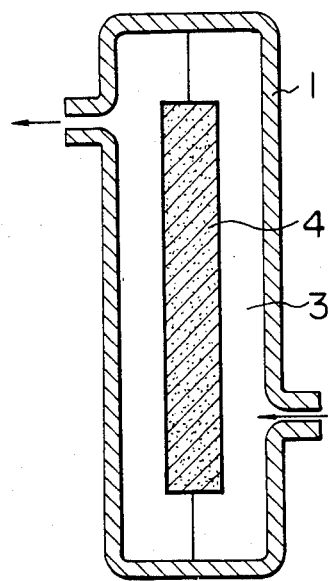

In the accompanying drawings,

FIGS. 1 to 3 show the graphs, indicating antimicrobial activities of the sensitizers for heterogeneous system photosensitive oxidation obtained in Examples of the present invention against bacteria, mold and yeast, respectively;

FIG. 4 a cross-sectional view of a water tank coated on its inner surface with an inhibitor in the form of a coated film comprising the sensitizer for heterogeneous system photosensitive oxidation of the invention;

FIG. 5 a cross-sectional view of a vessel having filled an inhibitor in the form of beads in the bed;

FIG. 6 a schematic view of one embodiment of the method according to the present invention in which plural filler beds are suspended in a water bath; and FIG. 7 a cross-sectional view of one example of a treating device having internally arranged the inhibiting part.

The sensitizer for heterogeneous system photosensitive oxidation of the present invention can exhibit noticeable effect for controlling activities of organisms when used in the presence of oxygen under exposure to visible light. It has not been elucidated so far why the sensitizer of the present invention has a remarkable function to control the activities of organisms. Such a function, however, is believed to be due to the action of singlet oxygen molecule or similar active species which is a molecule of oxygen activated by the energy of visible light and said sensitizer. As the photosensitive activity of said sensitizer is greater, namely with increase in the dissolved oxygen consumption value $\Delta DO$, the effect for controlling activities of organisms is better.

The effect for controlling activities of organisms mentioned in the present invention means giving such actions as killing, inhibition or proliferation, inhibition of growth, inhibition of germination or inactivation of living organisms. As the objective organisms, there may be mentioned a wide variety of organisms including viruses, bacteria, molds, yeasts, mycoplasmas, algae, plants, insects or others. Thus, the sensitizer of the present invention can be used in such fields of uses wherein bactericides, fungicides, antiseptic agents, pesticides, herbicides, proliferation inhibitors and growth inhibitors are presently available.

When the sensitizer for heterogeneous system photosensitive oxidation of the present invention is used for the purpose of controlling the activities of organisms, there may be used a light source as mentioned above which may suitably be selected depending on the intended uses and the forms of objects to be treated. As the oxygen source, pure oxygen is of course available, but naturally occurring oxygen, namely oxygen in the air or oxygen dissolved in liquids or solids, is enough to achieve the object of the present invention. It is also possible as a matter of course to supplement oxygen, if desired, by aeration or other methods for further improvement of efficiency.

The salient feature of the method for controlling the activities of organisms according to the present invention resides in the fact that its effect can be exhibited under completely heterogeneous conditions. Referring now to, for example, to the sterilization effect, chemical sterilization methods wherein various sterilizers are employed cannot effectively be applied, unless said sterilizers are homogeneously dissolved or dispersed in the system. Even if said sterilizers may be fixed on some carriers, namely by providing some heterogeneous system sterilizers, there can be exhibited no effect unless said sterilizers are eluted out into the system. To speak more precisely, when said sterilizers are completely fixed on the carriers, namely when said sterilizers are heterogeneous sterilizers from which no sterilizer is eluted, the sterlizing effect is completely lost. The effect of controlling activities of organisms possessed by the sensitizer for heterogeneous system photosensitive oxidation of the present invention is essentially different from the case as mentioned above. That is, the sensitizer per se does not possess the effect for controlling the activities of organisms, but such an effect is based on activated oxygen molecules formed by the action of visible light energy and said sensitizer. Accordingly, there is no decrease in its effect even if said sensitizing substance may be completely fixed on the carrier.

Thus, the effect of the sensitizer can permanently be maintained so long as said sensitizing substance is not decolored or discolored. As described previously in detail, the sensitizer for heterogeneous system photosensitive oxidation of the present invention has the physical and chemical stability. It is also very important from standpoint of environmental pollution that there is no sensitizing substance eluted out of the system. On behalf of this specific feature, there will be expected applications of the sensitizer of the present invention in infinite scope of uses which is not dreamt of in the prior art.

The light energy source to be used in the present invention may sufficiently be a visible light, which is more advantageous in safety as compared with radioactive rays or ultra-violet rays. What is more important is that a visible light is present universally in the natural world. Thus, the method of the present invention has another specific feature that no artifical light source equipment is necessary in some applications.

To describe about typical examples of the effect for controlling the activities of organisms mentioned in the present invention, they may be classified into three categories, depending on the object to be treated whether it is (1) gas phase, (2) liquid phase or (3) solid phase.

When the object to be treated is a gas phase, harmful microorganisms such as viruses, bacteria, molds or others floating in, for example, the air can be treated. Thus, it is possible to effect sterilization of the air which has been deemed as very difficult. To achieve such an object, the air can be circulated through a device filled with the sensitizer for heterogeneous system photooxidation, which may be shaped in any form suitably selected from those as previously described, in the presence of a visible light. In some cases, when the sensitizer takes a form in the shape of sheets, films, fibers or cloths, it may merely be exposed in the air without use of any specific device to exhibit sufficient effect.

When the object to be treated is a liquid phase, the sensitizer for heterogeneous system photo-sensitive oxidation shaped in various forms as mentioned above may be suspended, immersed or floated in the liquid to be treated in the presence of a visible light, whereby there can be obtained such effects as germicidal, fungicidal or proliferation inhibitory effect. Thus, there can be effected, for example, sterilization of sewage water, sterilization treatments in sea, rivers, lakes or ponds and reservoirs and also prevention of abnormal proliferation of mycoplasmas or algae. Accordingly, the present method can be very useful as a means for purification or re-use of water resources which have been at present great social problems and also as a means for prevention of red tide as occurring elsewhere in the sea, rivers, lakes or ponds.

When the object to be treated is a solid phase, preservative effect for prevention of decay or generation of molds can be obtained by, for example, wrapping foods with a sensitizer for heterogeneous system photosensitive oxidation which is shaped in a film. Also, during the growth of plants, said sensitizer for heterogeneous system photosensitive oxidation can be contacted with the plants, whereby inhibition of the plant growth, namely prevention of germination or herbicidal effect can be obtained. Furthermore, said sensitizer is useful as a multi-film having herbicidal function.

The method for controlling activities of organisms according to the present invention as described above is indeed epoch-making and applicable not only in the fields in which chemical substances such as sterilizers have been conventionally used, but also in such fields as purification of the sea and rivers or prevention of red tide, for which there was no applicable prior technique, to great social and industrial advantages.

In practicing control of organism activities by use of the sensitizers of the present invention as inhibitors, said inhibitor (sensitizer) may only be placed in the living circle of organisms in the presence of a visible light and oxygen. For better understanding, reference is made to the simplest embodiment of the invention as shown in FIG. 4, wherein the inner wall of the water tank 1 is coated with the inhibitor 2 of the present invention. In such a water tank, there is introduced a liquid to be treated 3 containing living organisms and said liquid is exposed to irradiation of a visible light such as the sunlight from outside in the presence of oxygen, whereby the activities of organisms in the liquid to be treated 3 can be controlled. To mention one example, by application of a coating as shown in FIG. 4 in an outdoor pool, sterilization of the pooled water can effectively be conducted. FIG. 5 shows inhibitors 2 in the form of beads filled in a vessel 4 which can be contacted with the external air. Any desired number of such filler beds can be arranged in the air under irradiation of a visible light to thereby perform effective sterilization of the air. FIG. 6 shows plural number of such filler beds suspended and immersed in the water bath 1. In this case, the filler beds may be replaced by inhibitors in the shape of cloths, tapes or nets. As one modification of the embodiment as shown in FIG. 6, the inhibitors of the present invention may only be located in natural water resources such as sea or lakes, whereby it is possible to prevent, for example, abnormal generation of red tide. FIG. 7 shows one example of a device capable of treating continuously a liquid to be treated (light source not shown). The inhibitor part 4 (e.g. filler bed as shown in FIG. 5) containing inhibitors is arranged in the vessel having inlet and outlet portions and the liquid to be treated is passed through the vessel in the direction of the arrow to effect treatment. In this case, the light source may be provided internally of the vessel, or alternatively the vessel may be made transparent to permit irradiation of light from outside. The oxygen may sometimes be sufficiently that dissolved in the liquid to be treated, but it is also possible to add oxygen compulsorily by aeration, etc.

As described above, the device to be used for practicing the method of the present invention may have a very simple constitution, comprising an inhibitor part containing the aforesaid inhibitors arranged so as to be contactable with the living circle of organisms to be treated and a means for irradiating a visible light arranged so as to be capable of irradiating said inhibitor part.

As mentiond above, the sensitizer for heterogeneous system photosensitive oxidation to be used for treatment of harmful organisms may preferably be prepared by supporting a sensitizer substance on a carrier having cation groups. Such a sensitizer is found to have a specific property to adsorb a large amount of organisms thereon. By use of such a sensitizer as adsorbent, water or air containing harmful organisms can only be contacted with said sensitizer to remove a part or all of the harmful organisms through adsorption even in the absence of a visible light. Under irradiation of a visible light in the presence of oxygen, the adsorbed organisms can be inactivated even to the extent of being killed. Thus, according to another embodiment of the method for treatment of harmful organisms by use of the sensitizer for heterogeneous system photosensitive oxidation of the present invention, a system containing such organisms is subjected to adsorption of the organisms on the sensitizer in the first step and then, on depletion of the adsorption activity, the sensitizer having organisms adsorbed thereon is activated by treatment with irradiation of light in the presence of air or oxygen. By use of the two step process as mentioned above, the sensitizer activated in the second step treatment can be used again in the first step. Accordingly, by repeating alternately the two steps combined, there can be established an entirely novel process for treatment of harmful organisms. The first specific feature of this process resides in enabling treatment of harmful organisms in places on which no irradiation of light is possible. The second feature resides in surprisingly high efficiency of the treatment. The third feature resides in that the sunlight may be made readily available as the visible light source, because the first step may be conducted at night or when it is rainy, while the second step can be performed in the day time, whereby continuous treatments through day and night can be made possible.

Another important field in which the sensitizer for heterogeneous photosensitive oxidation of the present invention can be applied is purification of water or air containing impurities. By use of the sensitizer of the present invention, highly efficient purification treatments are possible in purifying sewage water or industrial wastewater, making harmful substances harmless by oxidation, deodorizing substances with offensive odor or decoloration of colored substances. Examples of the contaminating substances, harmful substances or substances with offensive odor which can be removed by such treatments are organic compounds including olefinic compounds, diene type compounds polyene type compounds, aromatic compounds, heterocyclic compounds, alcohols, glycolic compounds, amine compounds, amide compounds, urea compounds, urethane compounds, phenol compounds, nitrile compounds, ketone compounds, ester compounds, aldehyde compounds, sulfur-containing compounds, etc., inorganic compounds including cyanate compounds, thiocyanate compounds, sulfite compounds, sulfide compound, thiosulfate compounds, etc. Furthermore, there are animal or vegetable wastes principally composed of protein compounds, carbohydrates compounds or fatty compounds of which structures cannot be identified, or decomposed products thereof. In carrying out purification of water or air containing these impurities by use of the sensitizer of the present invention, there may be used the same procedure and conditions as described previously with reference to the treatment of water or air containing harmful organisms.

The present invention is further illustrated with reference to the following Examples and Comparative examples, in which all parts and percentages are by weight unless otherwise noted.

Measurement of electron spectrum was conducted using Hitachi-124 Model spectrophotometer, the measurement of dissolved oxygen amount using Dissolved oxygen meter DO-1B Model (Toa Denpa Kogyo Co., Ltd.), and measurement of surface area using Surface area measuring instrument P-850 Model (Shibata Kagaku Co., Ltd.).

TEST METHODS (A) Measurement of dissolved oxygen consumption value (1) A sensitizing substance (5 mg) is supported on 50 mg of styrene-divinyl benzene copolymer (weight ratio=9:1) beads with particle diameters of 0.1 mm to 0.5 mm, which is in turn suspended in 500 ml of distilled water to be provided as a sample for measurement. Supporting of the sensitizing substance is performed according to any one of the methods as described in the specification.

(2) Light source

Using 500 W xenon lamp as light source, the luminosity at the light receiving face of the measuring vessel is set at 5,000 luxes by the standard white light having adjusted spectrum distribution by the filter as determined by JIS Z-8902.

(3) Measuring vessel

There is used a square vessel made of pyrex of 100 mm×100 mm×50 mm with only the light receiving face of 100 mm×100 mm being made transparent, other faces being intransparent in dark color.

(4) Measuring method

In a darkroom, 5 g of furfuryl alcohol was dissolved in the amount of the sample as determined in (1) and the dissolved oxygen value before the reaction $DO_0$ is set at 8 ppm at a temperature of 20° C. Said sample is filled in the measuring vessel of (3), followed by sealing. Under stirring with a magnetic stirrer, irradiation is effected from the light source of (2) for 10 minutes.

After irradiation, the dissolved oxygen value $DO_1$ is measured and the dissolved oxygen consumption value is calculated by the following formula:

$$\Delta DO = \frac{DO_0 - DO_1}{DO_0} \times 100$$

wherein $DO_0 = 8$ ppm.

(B) Light resistance evaluation of sensitizing substance

A cotton cloth is used as carrier and evaluation is conducted according to JISL-0841 by the direct sunshine method, the first light exposure method.

(C) Measurement of apparent surface area $A\ CO_2$

There is used a commercially available surface area measuring instrument according to the gas adsorption method, but carbon dioxide is used as the gas. By means of the above measuring instrument, Vm value is measured and the apparent surface area $A\ CO_2$ is calculated from the following formula:

$$A\ CO_2 = a \times \frac{Vm}{22,400} \times 6.02 \times 10^{23}$$

wherein $a$ is the cross-sectional area of carbon dioxide molecule (Å$^2$) and Vm is volume of carbon dioxide adsorbed (ml).

EXAMPLE 1

Preparation of various sensitizers for heterogeneous system photosensitive oxidation (1) Each 5 mg of the compounds shown in Table 1 was dissolved in 25 g of xylene and mixed with 50 g of the aforesaid polystyrene beads. After drying under vacuum at 100° C. for 10 hours, the mixture was suspended in 500 ml of distilled water for measurement of the dissolvved oxygen consumption value $\Delta DO$. The results are set forth in Table 4 together with the test values of light resistance and the results of $\lambda_{max}$ measured.

(2) Each 5 mg of the compounds shown in Table 2 was dissolved in 50 g of 98% conc. sulfuric acid and mixed with 50 g of the aforesaid polystyrene beads. After standing at 40° C. for 24 hours, each mixture was thrown into water, washed with an alkali and then with water, and suspended in 500 ml of distilled water for measurement of the dissolved oxygen consumption value $\Delta DO$. The results are set forth in Table 4 together with the light resistance values and the results of $\lambda_{max}$ measured.

(3) Each 5 mg of the compounds shown in Table 3, 0.5 g of caustic soda and 0.5 g of hydrosulfite were dissolved in 30 ml of distilled water and the resultant solution was subjected to sulfonation treatment with 98% conc. sulfuric acid at 40° C. for 24 hours. Each solution was then mixed with 50 g of the aforesaid polystyrene beads. After standing at 40° C. for 24 hours, each mixture was thrown into water for washing and then suspended in 500 ml of distilled water for measurement of dissolved oxygen consumption value $\Delta DO$. The results are shown in Table 4 together with light resistance values and the results of $\lambda_{max}$ measured.

TABLE 1

| Compound No. | Name of compounds |
|---|---|
| No. 1 | 1-hydroxy-4-aminoanthraquinone |
| No. 2 | N,N'—dibenzoyl-1,4-diaminoanthraquinone |
| No. 3 | 2,4-dinitro-4'-hydroxy diphenylamine |
| No. 4 | 4-nitrobenzeneazo-4'-aminobenzene |
| No. 5 | N—methyl-1,4-diaminoanthraquinone |
| No. 6 | coronene |
| No. 7 | 2-methylbenzeneazo-$\beta$-naphthylamine |

TABLE 2

| Compound No. | Name of compounds |
|---|---|
| No. 8 | 2,2'-diphenylanthraquinone dithiazole |
| No. 9 | dibenzopyrenequinone |
| No. 10 | dibromopyranthrone |
| No. 11 | 5,5'-dichloro-7,7'-dimethylthioindigo |
| No. 12 | dibromo-iso-violanthrone |
| No. 13 | dihydroanthraquinazine |
| No. 14 | flavanthrone |
| No. 15 | N—benzoyl-4-aminoanthrapyrimidine |
| No. 16 | phthalocyanine |
| No. 17 | copper-phthalocyanine |
| No. 18 | octachloro-copper-phthalocyanine |
| No. 19 | 2-chloro-4-nitrobenzeneazo-$\beta$-naphthol |
| No. 20 | 2,4-dinitrobenzeneazo-$\beta$-naphthol |

TABLE 3

| Compound No. | Name of compounds |
|---|---|
| No. 21 | dibromo-dibenzopyrenequinone |
| No. 22 | dibromo-anthanthrone |
| No. 23 | 5,5'-benzamidoanthraquinone carbazole |
| No. 24 | indigo |
| No. 25 | pyranthrone |
| No. 26 | 4-methyl-5,7-dichloro-4'-methyl-6-chloro-thioindigo |
| No. 27 | violanthrone |

TABLE 4

| Compound No. | $\Delta$DO value | Light resistance test values | $\lambda_{max}(nm)$ |
|---|---|---|---|
| No. 1 | 4.9 | 6 | 524 |
| No. 2 | 25.0 | 7 | 538 |
| No. 3 | 4.1 | 6 | 420 |
| No. 4 | 3.6 | 6 | 444 |
| No. 5 | 2.8 | 6 | 586 |
| No. 6 | 7.8 | 4 | 410 |
| No. 7 | 4.1 | 5 | 439 |
| No. 8 | 58.4 | 4 | 431 |
| No. 9 | 82.0 | 6 | 464 |
| No. 10 | 96.0 | 7 | 504 |
| No. 11 | 88.0 | 6 | 538 |
| No. 12 | 90.2 | 7 | 590 |
| No. 13 | 4.3 | 7 | 556 |
| No. 14 | 3.7 | 6 | 431 |
| No. 15 | 2.9 | 6 | 427 |
| No. 16 | 32.0 | 8 | 610 |
| No. 17 | 41.3 | 8 | 616 |
| No. 18 | 52.3 | 8 | 680 |
| No. 19 | 21.0 | 7 | 553 |
| No. 20 | 24.3 | 7 | 467 |
| No. 21 | 89.9 | 7 | 471 |
| No. 22 | 78.3 | 8 | 453 |
| No. 23 | 21.0 | 6 | 462 |
| No. 24 | 4.3 | 5 | 599 |
| No. 25 | 90.3 | 6 | 474 |
| No. 26 | 92.3 | 5 | 541 |
| No. 27 | 44.0 | 7 | 599 |

EXAMPLE 2

The compound No. 9 dibenzopyrenequinone used in Example 1, 100 mg, was dissolved in 100 g of 98% conc. sulfuric acid and then mixed with 100 g of styrene-methyl methacrylate-divinylbenzene copolymer beads (weight ratio=10:1:1) with average particle diameter of 0.3 mm. After standing for one hour at 40° C., the mixture was thrown into water, followed by washing with an alkali and with water, to prepare a sensitizer for heterogeneous system photosensitive oxidation. The sensitizer was suspended in 1.2 liter of distilled water containing 4.0 g of furfuryl alcohol and the reaction was carried out under oxygen atmosphere using an inner-irradiation type photochemical reactor (light source: 400 W sun-light lamp, produced by Toshiba Electric Co., Ltd.). The quantity of furfuryl alcohol disappeared was measured by gas chromatography (Hitachi-163 Model gaschromatograph) to obtain the result shown in Table 5.

TABLE 5

| Time of irradiation: (min.) | 5 | 10 | 15 | 20 |
|---|---|---|---|---|
| Quantity disappeared: (%) | 22 | 51 | 73 | 91 |

COMPARATIVE EXAMPLE 1

One hundred milligrams (100 mg) of the dibenzopyrenequinone powders used in Example 2 were suspended in 1.2 liter of distilled water containing 40 g of furfuryl alcohol and the reaction was carried out in the same reactor as used in Example 2. After irradiation for 5 minutes, 10 minutes, 15 minutes and 20 minutes, there was substantially no furfuryl alcohol disappeared.

EXAMPLE 3

The compound No. 22 dibromo-anthanthrone used in Exampe 1 (100 mg) was dissolved in 200 ml of distilled water containing 1 g of caustic soda and 1 g of hydrosulfite. A strip of a white cotton cloth of 300 mm×300 mm (kanakin No. 3) was dipped in the resultant solution at 40° C. and left to stand for one hour. After said immersion, the cloth was taken out and left to stand in the air for one hour, followed by washing with water, to obtain a sensitizer for heterogeneous system photosensitive oxidation.

The sensitizer was immersed in the reactor employed in Example 2 and the reaction was carried out under the same conditions. The rate of furfuryl alcohol disappeared was as shown in Table 6.

TABLE 6

| Irradiation time (min.) | 5 | 10 | 15 | 20 |
|---|---|---|---|---|
| Quantity disappeared (%) | 19 | 47 | 66 | 81 |

EXAMPLE 4

The compound No. 2 N,N'-dibenzoyl-1,4-diaminoanthraquinone (500 mg) used in Example 1 was dissolved in 100 ml of acetone and mixed with 100 g of 100-mesh silica gel powders. After standing for one hour, the mixture was thrown into water for washing to prepare a sensitizer for heterogeneous system photosensitive oxidation.

Using the same reactor and the reaction conditions as used in Example 2, the reaction was carried out, whereby the rate of furfuryl alcohol disappeared was as shown in Table 7.

TABLE 7

| Irradiation time (min.) | 5 | 10 | 15 | 20 |
|---|---|---|---|---|

TABLE 7-continued

| Quantity disappeared (%) | 7 | 12 | 18 | 23 |

EXAMPLE 5

In 300 ml of water were dissolved 7.2 g of β-naphthol and 1.8 g of caustic soda and a strip of cotton cloth (300 mm × 300 mm, Kanakin No. 3) was immersed in the resultant solution for 10 minutes. The above cotton cloth was dipped for 30 minutes in a solution of 0.75 g of 2-chloro-4-nitroaniline, 1.0 g of 35% hydrochloric acid and 0.5 g of sodium nitrite dissolved (at 10° C.) in 100 ml of water. After dipping, the cloth was thoroughly washed with water to prepare a sensitizer for heterogenous system photosensitive oxidation containing 2-chloro-4-nitrobenzeneazo-β-naphthol carried on a carrier.

The sensitizer was dipped in the same reactor as used in Example 2 to carry out the reaction under the same conditions. The rate of furfuryl alcohol disappeared was as shown in Table 8.

TABLE 8

| Irradiation time (min.): | 5 | 10 | 15 | 20 |
|---|---|---|---|---|
| Quantity disappeared (%): | 5 | 12 | 19 | 25 |

EXAMPLE 6

The sensitizer for heterogeneous system photosensitive oxidation used in Example 2 was recovered and, after washing with water, suspended in 1.2 liter of distilled water. The suspension was charged into the same reactor as used in Example 2 and irradiation was continued for 24 hours under oxygen atmosphere. There was no change detected in appearance in the sensitizer recovered after the irradiation. The sensitizer recovered was further suspended in distilled water containing 4.0 g of furfuryl alcohol and the reaction was carried out using the same reactor. The rate of furfuryl alcohol disappeared was as shown in Table 9.

COMPARATIVE EXAMPLE 2

A solution of 100 mg of Rose Bengal (light resistance test value=1) dissolved in 250 ml of distilled water was mixed with 100 g of ion-exchange resins (IRA-400; Rohm & Haas Co.) and the mixture was left to stand at room temperature for 24 hours.

After thorough washing of the mixture with water, there was prepared a sensitizer for heterogeneous system photosensitive oxidation. Using this sensitizer, the same procedure as in Example 6 was repeated whereby there was observed a noticeable discoloration after 24 hours of irradiation. In the experiment subsequently conducted, the rate of furfuryl alcohol disappeared was as shown in Table 9.

COMPARATIVE EXAMPLE 3

Comparative example 2 was repeated except that Rose Bengal was changed to Methylene Blue (light resistance test value=3) and the ion-exchange resins IRA-400 to IRC-200 (Rohm & Haas Co.). There was also a noticeable discoloration after 24 hours of irradiation and the rate of furfuryl alcohol disappeared in the experiment subsequently conducted was as shown in Table 9.

TABLE 9

| | | Irradiation time (min.): | | | |
|---|---|---|---|---|---|
| | | 5 | 10 | 15 | 20 |
| Quantity disappeared (%) | Example 6 | 23 | 53 | 71 | 93 |
| | Comparative example 2 | 1.5 | 2.2 | 3.1 | 3.9 |
| | Comparative example 3 | 2.1 | 2.9 | 3.7 | 4.0 |

EXAMPLE 7

A solution of 100 mg of the compound No. 11, 5,5'-dichloro-7,7'-dimethyl thioindigo used in Example 1 dissolved in 100 g of 98% conc. sulfuric acid was mixed with 100 g of styrene-methyl methacrylate-divinyl benzene copolymer beads (weight ratio=10:1:1) with average particle diameter of 0.3 mm. After standing at 40° C. for one hour, the mixture was thrown into water and washed with an alkali and with water to prepare a sensitizer for heterogeneous system photosensitive oxidation. The sensitizer was suspended in 1.2 liter of water containing 50 ppm of p-cresol and the reaction was carried out by charging said suspension into the same reactor as used in Example 2. The residual amount of p-cresol with the reaction was as shown in Table 10.

TABLE 10

| Irradiation time (min.): | 10 | 20 | 30 | 40 |
|---|---|---|---|---|
| Residual amount (ppm): | 31 | 20 | 11 | 3 |

After 40 minutes, the reaction mixture was filtered to give a filtrate which is completely colorless and transparent, indicating no change in appearance of the sensitizer for heterogeneous system photosensitive oxidation.

EXAMPLE 8

One gram of 1,4-diaminoanthraquinone was dissolved in 50 g of dimethylformamide and 5 g of acroyl chloride was added thereto. After the reaction at 30° C. for 5 hours, the reaction mixture was thrown into water and the precipitates were filtered and washed to give N,N'-diacroyl-1,4-diaminoanthraquinone. Five milligrams (5 mg) of this product were weighed and dissolved by mixing with 45 g of styrene, 5 g of divinylbenzene and 0.5 g of benzoyl peroxide. The resultant solution was subjected to suspension polymerization in 0.5% aqueous polyvinyl alcohol solution at 70° C. for 24 hours to give a copolymer in the form of beads with diameters from 0.1 mm to 0.5 mm at a yield of 100%. This sensitizer was found to have a ΔDO value of 19.0, a light resistance test value of 6 and $\lambda_{max}$ of 529 nm.

EXAMPLE 9

In a glass tube were sealed 25 g of anthracene and 12.5 g of sulfur powders and the reaction was carried out at 300° C. for 5 hours to give an olive-colored product. The product (5 mg) was dissolved in 30 ml of distilled water containing 0.5 g of caustic soda, 0.2 g of sodium sulfide and 0.3 g of hydrosulfite. The resultant solution was mixed with 50 g of styrene-divinylbenzene copolymer beads (weight ratio=9:1) with diameters of 0.1 mm to 0.5 mm which had been subjected to sulfonation treatment at 40° C. for 24 hours, and the mixture was left to stand in the air at 40° C. for 24 hours. After washing with water, there was obtained a sensitizer for heterogeneous system photosensitive oxidation. The sensitizer is found to have a ΔDO value of 58.3, a light resistance test value of 6 and $\lambda_{max}$ of 611 nm.

EXAMPLE 10

The compound No. 17 copper-phthalocyanine (100 mg) was supported by vapor deposition on an aluminum foil of 200 mm × 200 mm × 0.020 mm to prepare a sensitizer for heterogeneous system photosensitive oxidation colored in blue on its surface. This sensitizer was immersed in the same reactor as used in Example 2 to carry out the reaction under the same conditions. The rate of furfuryl alcohol disappeared was as shown in Table 11.

TABLE 11

| Irradiation time (min.): | 5 | 10 | 15 | 20 |
|---|---|---|---|---|
| Quantity disappeared (%): | 11 | 18 | 27 | 36 |

EXAMPLE 11

The sensitizer for heterogeneous system photosensitive oxidation containing the compound No. 9 dibenzopyrenequinone prepared in Example 2 (10 g) was suspended in one liter of water containing $3.5 \times 10^5$ cells/ml of a Gram-negative microorganism (*Escherichia coli* IFO-3301) and the standard white light of 3,500 luxes was irradiated over the water surface for 3 hours. The residual living microorganism during said irradiation were measured by the agar plate cultivation method to give the results as shown in FIG. 1(a), which shows a remarkable sterilizing effect.

COMPARATIVE EXAMPLE 4

Example 11 was repeated except that the compound No. 9 dibenzopyrenequinone (100 mg) was omitted. The results were also shown in FIG. 1(a).

EXAMPLE 12

A mixture comprising 50 g of styrene, 50 g of divinylbenzene, 100 g of 4-vinyl pyridine and 1 g of azobisisobutyronitrile was suspended in 800 ml of an aqueous 0.5% polyvinyl alcohol solution and polymerized at 65° C. for 10 hours to give a polymer in the form of beads with average diameter of 0.25 mm. The polymer beads were treated with a 6N sulfuric acid at room temperature for 6 hours. Then, into 100 g of 98% sulfuric acid containing 100 mg of the compound No. 10 dibromopyranthrone used in Example 1 dissolved therein, the aforesaid polymer beads were added. The mixture was left to stand at 40° C. for 24 hours, followed by washing with water, to prepare a sensitizer for heterogeneous system photosensitive oxidation having cation groups.

The above sensitizer for heterogeneous system photosensitive oxidation (10 g) was suspended in one liter of water containing $2.2 \times 10^5$/ml of a Gram-negative microorganism (*Escherichia coli* IFO-3301) and the standard white light of 3,500 luxes was irradiated over the water surface for 3 hours. The residual living microorganisms during said irradiation were measured similarly as in Example 11 to give the results as shown in FIG. 1(1).

COMPARATIVE EXAMPLE 5

Example 12 was repeated except that there was used no compound No. 23 dibromopyranthrone. The results are also shown in FIG. 1(b).

EXAMPLE 13

A strip of a commercially available 6-Nylon cloth (N-1003) of 300 mm × 300 mm was immersed in an aqueous 25% sulfuric acid solution at 25° C. for 15 minutes, then washed with water and dried.

The compound No. 12 dibromo-iso-violanthrone used in Example 1 (150 mg) was dissolved in 200 ml of distilled water containing 1 g of caustic soda and 1 g of hydrosulfite. In the resultant solution was dipped the above 6-nylon cloth subjected to sulfuric acid treatment at 40° C. for one hour. The cloth was taken out after said dipping and left to stand in the air for one hour, followed by washing with water, to obtain a sensitizer for heterogeneous system photosensitive oxidation having cation groups. The sensitizer was suspended in one liter of water containing $9.7 \times 10^7$/ml of a Gram-negative microorganism (*Escherichia coli* IFO-3301) and the standard white light of 3,500 luxes was irradiated over the water surface. The changes in number of residual living organisms were measured similarly as in Example 11 to obtain the results shown in Table 12.

EXAMPLE 14

Example 13 was repeated except that 10 g of commercially available ion-exchange resins (Amberlite IRA-938: anion exchange resins, produced by Rohm & Haas Co.) was used as carrier in place of the 6-nylon cloth subjected to the sulfuric acid treatment. The results are also shown in Table 12.

EXAMPLE 15

Example 13 was repeated except that 10 g of of aluminum silicate (400-mesh) was used as carrier in place of the 6-nylon cloth subjected to the sulfuric acid treatment. The results are also shown in Table 12.

COMPARATIVE EXAMPLE 6

A mixture comprising 50 g of styrene, 50 g of divinylbenzene, 100 g of p-chloromethyl stryene and 1 g of azobisisobutyronitrile was subjected to suspension polymerization in 800 ml of an aqueous 0.5% polyvinyl alcohol solution at 70° C. for 24 hours to obtain polymer beads with average diameter of 0.15 mm. The polymer beads (100 g) and 10 g of Rose Bengal were mixed with 500 ml of dimethylformamide and the reaction was conducted under heating at 60° C. for 48 hours. After the reaction, filtration and washing with water were repeated to give a sensitizer for heterogeneous system photosensitive oxidation. Using '0 g of this sensitizer, evaluation of its performance was conducted under the same conditions as in Example 13 to obtain the results as shown in Table 12.

COMPARATIVE EXAMPLE 7

One mg of a commercially available sterilizer monosodium dichloroisocyanurate was dissolved in one liter of water containing $9.7 \times 10^4$/ml of a Gram-negative microorganism (*Escherichia coli* IFO-3301) (concentration of the sterilizer = 1 ppm). The changes in number of the living microorganism were measured by the same method as in Example 11 to give the results as shown in Table 12.

TABLE 12

|  | 0 minute | 30 minutes | 60 minutes |
|---|---|---|---|
| Example 13 | $9.7 \times 10^4$/ml | 0/ml | 0/ml |
| Example 14 | $9.7 \times 10^4$/ml | 2/ml | 0/ml |

TABLE 12-continued

| | 0 minute | 30 minutes | 60 minutes |
| --- | --- | --- | --- |
| Example 1.5 | $9.7 \times 10^4$/ml | 5/ml | 0/ml |
| Comparative example 6 | $9.7 \times 10^4$/ml | $5 \times 10^2$/ml | 125/ml |
| Comparative example 7 | $9.7 \times 10^4$/ml | $3 \times 10^2$/ml | 271/ml |

EXAMPLE 16

The sensitizer for heterogeneous system photosensitive oxidation employed in Example 12 (10 g) was suspended in one liter of a culture broth for algae (ASP-2) containing bluish algae and diatom and the suspension was left to stand in the outdoors under aeration with an air adjusted to contain 1% of carbon dioxide. After one month, there was observed no proliferation of algae at all.

COMPARATIVE EXAMPLE 8

Example 16 was repeated except that no dibromopyranthrone (100 mg) was used. After one week, there was observed noticeable proliferation of algae.

EXAMPLE 17

The sensitizer for heterogeneous system photosensitive oxidation as prepared in Example 8 (10 g) was suspended in one liter of water containing $2.2 \times 10^5$/ml of a mold (*Trichoderma viride* IFO-4847) and the standard white light of 3,500 luxes was irradiated over the water surface for 3 hours. The residual living microorganism cells were measured similarly as in Example 11 to obtain the results as shown in FIG. 2.

COMPARATIVE EXAMPLE 9

Example 17 was repeated except that the sensitizer contained no N,N'-diacroyl-1,4-diaminoanthraquinone to obtain the results as shown in FIG. 2.

EXAMPLE 18

The sensitizer for heterogeneous system photosensitive oxidation as prepared in Example 3 was dipped in one liter of water containing $1.9 \times 10^5$/ml of yeast (*Candida albicans* IFO-0583) and irradiated with light similarly as in Example 11. The number of residual living microorganisms was measured in the same manner as in Example 11 to obtain the results as shown in FIG. 3.

COMPARATIVE EXAMPLE 10

Example 18 was repeated except that there was used no dibromo-anthanthrone to obtain the results as shown in FIG. 3.

EXAMPLE 19

The compound No. 2 N,N'-dibenzoyl-1,4-diaminoanthraquinone (1.5 g) used in Example 1 was dissolved in 100 g of a commercially available acrylic clear lacquer. The solution was coated on a commercially available ply-wood (300 mm × 300 mm × 3 mm) to obtain a coated film colored in reddish violet. One platinum loop of a mold (*Trichoderma viride* IFO-4847) was dispersed in 100 ml of a culture broth for mold. The resultant dispersion was applied by a micropipette on four spots on the above coated film at intervals of 100 mm. This sample was left to stand for 7 days in a thermostatical humidistat maintained at a temperature of 30° C. and a humidity of 85% under a luminosity on the sample surface set at 350 luxes. The periodical changes are as shown in Table 13.

COMPARATIVE EXAMPLE 11

Example 19 was repeated except that N,N'-dibenzoyl-1,4-diaminoanthraquinone was omitted to give the results as shown in Table 13.

TABLE 13

| | 2 days | 3 days | 5 days | 7 days |
| --- | --- | --- | --- | --- |
| Example 19 | no change | no change | no change | no change |
| Comparative example 11 | black spot partly formed | black spots formed | vigorous proliferation | vigorous proliferation |

EXAMPLE 20

In 100 g of 98% of conc. sulfuric acid was dissolved 250 mg of the compound No. 11, 5,5'-dichloro-7,7'-dimethyl thioindigo as used in Example 1. The resultant solution was mixed with 100 g of a styrenemethyl methacrylate-divinylbenzene copolymer beads (weight ratio = 10:1:1) with average particle diameter of 0.1 mm, and the mixture was left to stand at 40° C. for one hour. Then, the mixture was thrown into water, followed by washing with an alkali and with water, to obtain a sensitizer for heterogeneous system photosensitive oxidation.

A ground with an area of 2 m × 2 m was divided into two areas of 2 m × 1 m. Over one of the divided areas, there was sprayed the total amount of the above sensitizer for heterogeneous system photosensitive oxidation. After two months, there was abundant growth of weeds in the non-sprayed area, while there was no growth of weeds in the sprayed area at all.

EXAMPLE 21

The same sensitizer for heterogenous system photosensitive oxidation as used in Example 20 was suspended in an amount of 50 g in one liter of a pooled water containing mosquito larvae (*Culex tritaeniorhynchus*) and the suspension was left to stand in a room set at a luminosity on the water surface of 750 luxes. The percentages of the survived larvae and of the hatched larvae, respectively, are as shown in Table 14.

COMPARATIVE EXAMPLE 12

Example 21 was repeated except that 250 mg of 5,5'-dichloro-7,7'-dimethyl thioindigo was not used, whereby the results shown in Table 14 were obtained.

TABLE 14

| | Percentage of survival (%) | | | Percentage hatched (%) |
| --- | --- | --- | --- | --- |
| | 1 day | 3 days | 7 days | |
| Example 21 | 28 | 4 | 0 | 0 |
| Comparative example 12 | 95 | 93 | 93 | 88 |

EXAMPLE 22

In 200 ml of distilled water containing 1 g of caustic soda and 1 g of hydrosulfite, 250 mg of the compound No. 25 pyranthrone was dissolved. In the resultant solution was immersed a commercially available cellophane film of 300 mm × 300 mm (no treatment; thickness = $15\mu$) at 40° C. for one hour. The cellophane film was taken out after said immersion and left to stand in the air for one hour, followed by washing with water, to obtain a sensitizer for heterogeneous system photosensitive oxidation. Using this film, meat was wrapped therein. The wrapped meat was left to stand under the conditions of 30° C. and a luminosity of 350 luxes for one week to obtain the results as shown in Table 15.

COMPARATIVE EXAMPLE 13

Example 22 was repeated except that 250 mg of pyranthrone was not used to obtain the results as shown in Table 15.

TABLE 15

|  | After one day | After 7 days |
| --- | --- | --- |
| Example 22 | no change | no change |
| Comparative example 13 | putrid smell formed | excessive putrid smell |

EXAMPLE 23

A commercially available polystyrene film (thickness=50μ) was dipped in a mixture for crosslinking comprising para-formaldehyde, acetic acid and sulfuric acid (5 parts:25 parts:70 parts) and crosslinking reaction was effected at 75° C. for 3 hours to crosslink the polystyrene to make it insoluble. Then, the crosslinked film was dipped in a solution comprising chloromethyl ether and stannic chloride (85:15) to carry out the reaction at 40° C. for one hour and 20 minutes. After the reaction, the product was washed with 10% hydrochloric acid, distilled water and acetone. The thus chloromethylated film was aminated at 40° C. for one hour and 20 minutes by dipping in a 30% aqueous trimethylamine solution. Subsequently, 0.5 part of the compound No. 2 N,N'-dibenzoyl-1,4-diaminoanthraquinone was dissolved in 50 parts of acetone. The above treated film was dipped in the resultant solution and left to stand at 40° C. for 10 hours, followed by drying on the air, to obtain a sensitizer carried on a carrier having cation groups.

Five sheets of the above film sensitizer (1 m×2 m) were immersed vertically into a water storage tank of 15 m×10 m with the depth of 2.5 m. They were left to be immersed in the tank during the night and taken out from the tank for exposure to the sunlight in the day time under the sunshine. This procedure was repeated continuously for 20 days. Sampling of the stored water was performed once per day for measurement of miscellaneous microorganism cells by the agar culture method. The results are shown in Table 16.

COMPARATIVE EXAMPLE 14

Example 23 was repeated, but there was employed a film prepared according to the same method as in Example 23 except for using no N,N'-dibenzoyl diaminoanthraquinone. The results are also shown in Table 16.

TABLE 16

| | Microorganism cells in the water tested (cells/ml) | | | | |
| --- | --- | --- | --- | --- | --- |
| | 1st day | 3rd day | 5th day | 7th day | 10th day |
| Example 23 | 5 | 1 | 0 | 2 | 0 |
| Comparative example 14 | $5 \times 10^2$ | $3 \times 10^2$ | $4 \times 10^2$ | $7 \times 10^2$ | $8 \times 10^2$ |

EXAMPLE 24

In 200 parts of distilled water containing 1 part of caustic soda and 1 part of hydrosulfite was dissolved 0.1 part of the compound No. 23 dibromodibenzopyrenequinone as used in Example 1. A white cotton cloth (Kanakin No. 3) was dipped in the resultant solution and left to stand at 40° C. for one hour. After dipping, the cloth was taken out and left to stand in the air for one hour. Then, the cloth was washed with water and dried on air. The thus treated cloth was further immersed in an aqueous 10% β-γ epoxypropyl trimethylammonium chloride solution at 35° C. for one hour. Then, the cloth was taken out and dried on air at 35° C. to 40° C., followed by heat treatment at 110° C., to give a sensitizer carried on a carrier having cation groups.

In a pool with dimensions of 25 m×12 m×15 m equipped with a circulator, there were provided two series of filter tanks equipped with change-over cocks. In each of the filter tanks, 15 sheets of the above cloth-like sensitizers (50 cm×50 cm) superposed on each other were assembled as filter material.

Using one series of the filter tanks, circulation of water was conducted at the flow rate of 150 m³/hour, followed by change-over to the other series by means of the change-over cock to continued the operation. In the meantime, used filter materials were exposed to the sunlight in the day time and thereafter filled again in the filter tank. The above procedure was repeated, thus using two series of the filter tanks alternately each for 24 hours, to continue the running for 14 days. In every 3 hours, sampling of water was performed for 8 times per day for testing E. coli microorganisms. During said running, there was added no chemical such as a sterilizer into the pool at all.

Using 10 ml of water to be tested, the number of living E. coli microorganisms was measured by the agar culture method. Table 17 shows the results, indicating the number of the tests among 8 per day wherein there was detected at least one/10 ml of E. coli.

COMPARATIVE EXAMPLE 15

Using cloths prepared by the same method as in Example 24 except for using no compound No. 23 dibromo-dibenzopyrenequinone, evaluation was conducted under totally the same conditions as in Example 4 to obtain the results as shown in Table 17.

TABLE 17

| | 1st day | 3rd day | 5th day | 10th day | 14th day |
| --- | --- | --- | --- | --- | --- |
| Example 24 | 0 | 0 | 0 | 0 | 0 |
| Comparative example 15 | 1 | 8 | 8 | 8 | 8 |

EXAMPLE 25

According to the same procedure as described in Example 24 except for changing the compound No. 23 dibromo-dibenzopyrenequinone to the compound No. 11 dibenzopyrenequinone and the cotton cloth to 6-nylon cloth, there was prepared a cloth-like sensitizer.

Five sheets of the above cloth-like sensitizer (50 cm×50 cm) were superposed on each other and provided for use as the filter for an air-conditioner for use in aseptic laboratory with dimensions of 4 m×7 m×3 m capable of maintaining thermostatical and humidistatical conditions under circulation of the air. Running was continued for 24 hours under the flow rate of 40 m³/hour. After 24 hours, a new set of five sheets of the filter was filled to replace the used filters. While continuing the running, the used filters were subjected to treatment under 20,000 luxes by means of a metal halide lamp for 2 hours. This procedure was repeated by using alternately the two set of filters to perform continuous running for 14 days. One time in a day during said running, the number of miscellaneous microorganisms contained in the aseptic room was measured by collecting microorganisms using an air-sampler on a membrane, followed by cultivation. The results are shown in Table 18.

COMPARATIVE EXAMPLE 16

Example 25 was repeated except for effecting no irradiation of light to obtain the results as shown in Table 18.

TABLE 18

| | Miscellaneous microorganisms in the aseptic room (cells/100 liter) | | | | |
|---|---|---|---|---|---|
| | 1st day | 4th day | 7th day | 10th day | 14th day |
| Example 25 | 0 | 0 | 0 | 0 | 0 |
| Comparative example 16 | 10 | 20 | 20 | 30 | 30 |

EXAMPLE 26

In 15 liter of water containing 150 ppm of cyanides, there was dispersed 160 g of the sensitizer as prepared in Example 2. The dispersion was left to stand in the outdoors under aeration for 7 hours. During this period, the luminosity of the sunlight on the water surface in the above reactor varied in the range from 86,000 luxes at the maximum to 9,000 luxes at the minimum.

After the above oxidation treatment, the concentration of cyanides was determined according to the method of JIS K 0102 to be 7.5 ppm.

EXAMPLE 27

In 3.6 liters of the filthy water for test having the water quality test values as shown in Table 19 was suspended 150 g of the sensitizer for heterogeneous system photosensitive oxidation as prepared in Example 2. The suspension was placed in the same reactor as used in Example 2 and the treatment was effected under oxygen atmosphere for 2 hours. After the treatment, followed by filtration of the reaction mixture, the filtrate was subjected to the water quality test according to the method as defined by JIS K0102. The results are shown in Table 19.

EXAMPLE 28

Example 27 was repeated, but the sensitizer for heterogeneous system photosensitive oxidation as prepared in Example 4 was used to obtain the results as shown in Table 19.

COMPARATIVE EXAMPLE 17

In water containing one part of Methylene Blue (light resistance test value=3), there was added 150 g of a commercially available ion-exchange resin (Amberlite IRC-84; Rohm & Haas Co.) and the mixture was left to stand at room temperature for 24 hours. After filtration and washing with water, there was prepared a sensitizer for heterogeneous system photosensitive oxidation.

By use of this sensitizer, the same procedure as in Example 27 was repeated to give the results as shown in Table 19.

COMPARATIVE EXAMPLE 18

Example 4 was repeated except for omitting N,N'-dibenzoyl-1,4-diaminoanthraquinone. The resultant powders were used to repeat the same procedure as described in Example 27. The results are also shown in Table 19.

EXAMPLE 29

In 200 g of water in which 0.5 g of the compound No. 25 pyranthrone, 1 g of caustic soda and 1 g of hydrosulfite were dissolved, there was added 150 g of a styrene-divinylbenzene microporous gel (Amberlite XAD-4, trade mark, produced by Rohm & Haas, having an apparent surface area A $CO_2$ 780 m²/g) and the mixture was left to stand at 40° C. for one hour. Then, the product was filtered and washed under running water for one hour to prepare a sensitizer for heterogenous system photosensitive oxidation.

Example 27 was repeated by using this sensitizer to obtain the results as shown in Table 19.

TABLE 19

| | Before treatment | Example 27 | Example 28 | Example 29 | Comparative example 17 | Comparative example 18 |
|---|---|---|---|---|---|---|
| Appearance | slightly turbid, pale yellow | transparent, colorless | transparent, colorless | transparent, colorless | colored in blue | pale yellow |
| Odor | slight odor of chemical | odorless | odorless | odorless | odorless | slight odor of chemical |
| pH | 6.8 | 6.9 | 7.2 | 6.9 | 5.9 | 6.8 |
| COD (ppm) | 420 | 11 | 31 | 5 | 225 | 399 |
| Mass of floating matter (ppm) | 27 | less than 10 | less than 10 | less than 10 | 19 | 29 |
| n-hexane extract (ppm) | 16 | less than 2.0 | less than 2.0 | less than 2.0 | 9 | 14 |
| Content of phenols (ppm) | 5 | ND | ND | ND | 2 | 5 |
| Content of cyanides | 3 | ND | ND | ND | ND | 3 |

TABLE 19-continued

| | Before treatment | Example 27 | Example 28 | Example 29 | Comparative example 17 | Comparative example 18 |
|---|---|---|---|---|---|---|
| (ppm) | | | | | | |

(Note)
ND: not detected

EXAMPLE 30

The cloth-like sensitizer (30 cm×50 cm) for heterogeneous system photosensitive oxidation as prepared in Example 3 was filled in the same photochemical reactor as used in Example 2. While circulating the air containing 5 ppm of methyl mercaptan, irradiation of the light was effected for 3 hours. The methyl mercaptan content in the air after the treatment was measured to be less than 0.1 ppm and there was no odor detected in the air.

We claim:

1. A heterogeneous system photosensitive oxidation sensitizer prepared by the steps comprising:
   (i) providing a coloring substance having a light resistance test value of from Rating No. 4 to No. 8 and a substance capable of serving as a solvent medium for said coloring substance;
   (ii) allowing the coloring substance to dissolve or molecularly disperse completely in the solvent medium, the formation of the solution or the molecular dispersion resulting in the coloring substance becoming photosensitively active; and
   (iii) allowing the photosensitively active coloring substance to be absorbed on a carrier therefor so that the resulting sensitizer has a photosensitivity as $\Delta DO$ value of at least 0.5, determined by dissolving a predetermined amount of the sensitizer in water having a predetermined oxygen concentration and applying a predetermined intensity of irradiation to the resulting solution.

2. A sensitizer according to claim 1, wherein the carrier is in the form of powders.

3. A sensitizer according to claim 1, wherein the carrier is in the form of granules.

4. A sensitizer according to claim 1, wherein the coloring substance is an aromatic ketone compound or a derivative thereof.

5. A sensitizer according to claim 1, wherein the carrier is in the form of powders and the coloring substance is an aromatic ketone compound or a derivative thereof.

6. A sensitizer according to claim 1, wherein the carrier is in the form of granules and the coloring substance is an aromatic ketone compound or a derivative thereof.

* * * * *